US012599774B2

(12) United States Patent
Delisle et al.

(10) Patent No.: US 12,599,774 B2
(45) Date of Patent: Apr. 14, 2026

(54) POWER CHARGING FOR MODULAR MEDICAL DEVICES

(71) Applicant: KONINKLIJKE PHILIPS N.V., Eindhoven (NL)

(72) Inventors: Norman Maurice Delisle, Manchester, MA (US); Patrick Guiney, Concord, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 564 days.

(21) Appl. No.: 14/980,364

(22) Filed: Dec. 28, 2015

(65) Prior Publication Data

US 2016/0184598 A1    Jun. 30, 2016

Related U.S. Application Data

(60) Provisional application No. 62/097,782, filed on Dec. 30, 2014.

(51) Int. Cl.
| | |
|---|---|
| *A61N 1/39* | (2006.01) |
| *H02J 7/34* | (2006.01) |
| *A61N 1/36* | (2006.01) |

(52) U.S. Cl.
CPC ......... *A61N 1/3975* (2013.01); *A61N 1/3904* (2017.08); *A61N 1/3925* (2013.01); *H02J 7/342* (2020.01); *A61B 2560/0214* (2013.01); *A61N 1/3603* (2017.08)

(58) Field of Classification Search
CPC .... A61N 1/378; A61N 1/3787; A61N 1/3975; A61N 1/39904; A61N 1/3925; A61N 1/3603; A61N 1/3904; A61B 2560/0214; H02J 7/342
See application file for complete search history.

(56) References Cited

U.S. PATENT DOCUMENTS

| | | | |
|---|---|---|---|
| 5,733,313 A * | 3/1998 | Barreras, Sr. ........ | A61N 1/3787 607/33 |
| 6,591,135 B2 | 7/2003 | Bayer et al. | |
| 8,751,010 B2 * | 6/2014 | Rondoni ............. | A61N 1/3787 607/33 |
| 8,788,038 B2 | 7/2014 | Neumiller et al. | |
| 2007/0170887 A1 | 7/2007 | Harguth et al. | |
| 2008/0221397 A1 | 9/2008 | Mcmahon et al. | |
| 2012/0158075 A1 | 6/2012 | Kaib et al. | |
| 2014/0142647 A1 | 5/2014 | Mcmahon et al. | |

* cited by examiner

*Primary Examiner* — Tammie K Marlen

(57) ABSTRACT

A modular medical device (e.g., modular defibrillator/monitor) employs a primary medical module including a primary power source (e.g., battery(ies) and/or power supply) for powering an execution of a primary medical task assigned to the primary medical module (e.g., electrical therapy), and a remote medical module including a remote power source (e.g., battery(ies) and/or power supply) for powering an execution of a remote medical task assigned to the remote medical module (e.g., patient parameter monitoring). In operation, primary medical module ascertains if primary power source has sufficient power or insufficient power for the execution of the primary medical task, and remote medical module controls a charging of remote power source by primary power source if primary medical module ascertains primary power source has sufficient power for the execution of the primary medical task.

9 Claims, 2 Drawing Sheets

POWER CHARGING FOR MODULAR MEDICAL DEVICES

This application claims priority to U.S. application Ser. No. 62/097,782, filed on Dec. 30, 2014, the entire disclosure of which is incorporated herein by reference.

FIELD OF THE INVENTION

The present invention generally relates to power charging between a remote medical module (e.g., a monitor module) and a primary medical module (e.g., a therapy module) of a modular medical device (e.g., a modular defibrillator/monitor). The present invention specifically relates to a battery charging of the remote medical module by the primary medical module that is initiated by the remote medical module under specific operational conditions of the remote medical module and/or the primary medical module.

BACKGROUND OF THE INVENTION

Portable defibrillator/monitors are used in hospitals and outside hospitals for emergency medical care. These devices incorporate one or more vital signs monitoring parameters such as, for example, electrocardiogram ("ECG"), pulse oximetry ("SpO2"), non-invasive blood pressure ("NIBP"), exhaled (end tidal) carbon dioxide ("EtCO2"), temperature and invasive blood pressure ("IBP"). These devices further incorporate electrical therapy delivery capabilities such as, for example, a defibrillation shock, synchronized cardioversion and transcutaneous pacing.

In a modular version of a portable defibrillator/monitor, all or part of the patient measurement capability is primarily provided by a measurement module that is separable from a therapy module that provides high energy therapy delivery. The measurement module is typically smaller and lighter than the therapy module, which houses larger and heavier electrical components needed for the high energy therapy delivery. Because the measurement module is small and light, the measurement module can be handled easily and may be placed on a stretcher with the patient to provide continuous monitoring of the patient's vital parameters as the patient is transported.

For example, a commercially available modular defibrillator/monitor known as the corpuls[3] may be split into a monitoring unit, a patient box and a defibrillator/pacer unit. When split apart, these modules are capable of wireless communication with the patient box providing a display and user interface controls for both the monitoring unit and the defibrillator/pacer unit. More particularly, the corpuls[3] uses an external power supply for battery charging of the modules. In addition, when docked, a module is capable of operating from power supplied by batteries of one of the other modules without a charging of the docked module's batteries. Consequently, identical batteries are typically used by each module.

By further example, U.S. Pat. No. 8,788,038 B2 describes an external defibrillator employing a base defibrillator module having capabilities to serve as a primary medical module for controlling a powering and charging of a battery of a separable measurement pod (i.e., the remote medical module). Specifically, the base defibrillator module determines when the measurement pod's battery is to be charged based on the base battery's power condition and the measurement pod's battery power condition.

SUMMARY OF THE INVENTION

To improve upon the prior art, the present invention provides a power charging scheme for a modular medical device involving a remote medical module conditionally controlling a power charging of the remote medical module by a primary medical module. A primary condition is the primary medical module having sufficient power to battery charge the remote medical module in addition to executing medical task(s) assigned to the primary medical module. An optional condition is the remote medical module having insufficient power to execute task(s) assigned to the remote medical module.

For example, a modular defibrillator/monitor may involve a monitoring module conditionally controlling a power charging of the monitoring module by a therapy module with the conditions (1) including the therapy module having sufficient power to power charge the monitoring module in addition to executing an electrical therapy task assigned to the therapy module, and (2) optionally including the monitoring module having insufficient power to execute a patient parameter monitoring task assigned to the monitoring module.

This new and unique charging scheme may be implemented in many forms for modular medical devices including, but not limited to, commercially available modular medical devices (e.g., the corpuls[3]) and for newly developed or in development modular medical devices.

One form of the present invention is a modular medical device (e.g., modular defibrillator/monitor) for a modular execution of a plurality of medical tasks. The modular medical device employ a primary medical module including a primary power source for powering an execution of a primary medical task assigned to the primary medical module (e.g., an electric therapy module), and a remote medical module including a remote power source for powering an execution of a remote medical task assigned to the remote medical module (e.g., a patient parameter monitoring module). In operation, the primary medical module monitor whether the primary power source has sufficient power or insufficient power for the execution of the primary medical task assigned to the primary medical module, and the remote medical module controls a charging of the remote power source by the primary power source if the primary medical module ascertains the primary power source has sufficient power for the execution of the primary medical task assigned to the primary medical module.

For purposes of the present invention, terms of the art including, but not limited to, "modular medical device", "medical module", and "medical task" are to be broadly interpreted as known in the art of the present invention and exemplary described herein.

Examples of the medical modules usable for the present invention include, but are not limited to, electric therapy modules, patient parameter monitoring modules, and therapy coaching modules.

For purposes of the present invention, the term "primary" and "remote" as applied to the term "medical module" and "medical task" and are utilized for purposes of distinguishing between modules and tasks and is therefore not limiting as to the structural configuration of the any particular medical module as employed by the present invention.

For purposes of the present invention, the term "power source" broadly encompasses any type of electrical battery or electronic device utilized by the medical industry to power a module. Examples of a power source include, but are not limited to, a rechargeable battery, a non-rechargeable battery and a power supply.

The foregoing form and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

DETAILED DESCRIPTION OF THE PREFERRED EMBODIMENTS

To facilitate an understanding of the present invention, exemplary embodiments of the present invention will be provided herein directed to an implementation of a modular medical device employing a primary medical module and a remote medical module in the form of a modular defibrillator/monitor employing a primary therapy module and a remote monitor module. Nonetheless, those having ordinary skill in the art will appreciate who to make and use the present invention for numerous modular medical devices employing various medical modules for the execution of various medical tasks in accordance with the inventive principles of the present invention as exemplarily described herein.

For purposes of the present invention, terms of the art including, but not limited to, "display, "user interface", "patient parameter monitoring", "electrical therapy", "power interface", "power source", "base station" and "docking station" are to be broadly interpreted as known in the art of the present invention and exemplary described herein.

For purposes of the present invention, the term "controller" broadly encompasses all structural configurations of an application specific main board or an application specific integrated circuit housed within or linked to a medical module for controlling an application of various inventive principles of the present invention as subsequently described herein. The structural configuration of the controller may include, but is not limited to, processor(s), computer-usable/computer readable storage medium(s), an operating system, executable software/firmware, peripheral device controller(s), slot(s) and port(s). Examples of a housing form of a module include, but are not limited to, standard module housing (e.g., housing for the modules of the corpuls³) and a portable computer (e.g., a tablet or a laptop).

Figure 1:
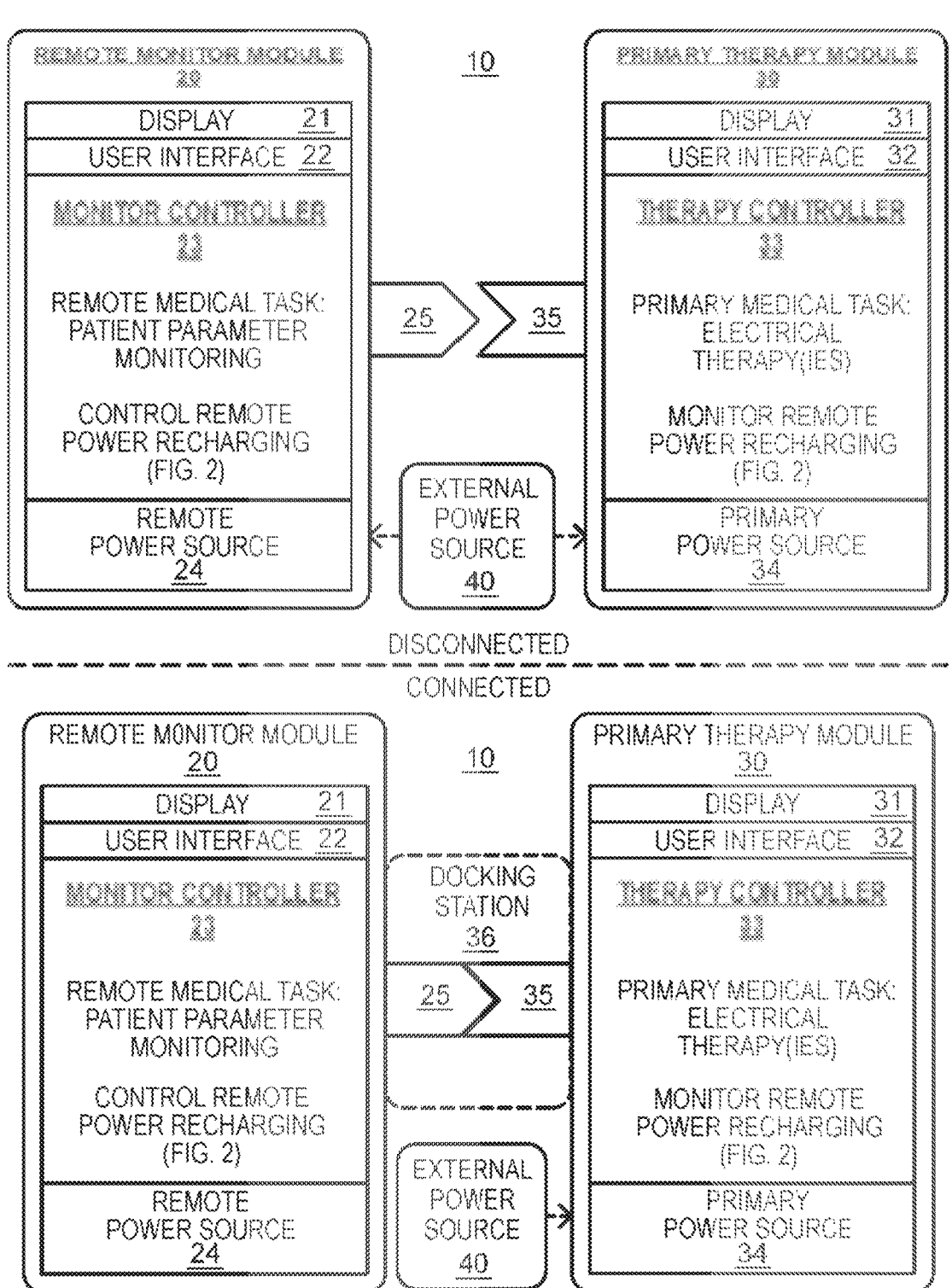
FIG. 1 illustrates exemplary embodiments of a primary medical module and a remote medical module in accordance with the inventive principles of the present invention.

Referring to FIG. 1, generally, a modular defibrillator/monitor 10 employs a remote monitor module 20 that may be power connected to a primary therapy module 30. Remote monitor module 20 has remote power source 24 for self-powering an operation of remote monitor module 20 in executing known patient parameter monitoring technique(s) including, but not limited to, measurements of an electrocardiogram ("ECG"), a pulse oximetry ("SpO2"), a non-invasive blood pressure ("NIBP"), an exhaled (end tidal) carbon dioxide ("EtCO2"), a temperature and an invasive blood pressure ("IBP"). Primary therapy module 30 has a primary power source 34 for self-powering an operation of primary therapy module 30 in executing electrical therapy technique(s) including, but not limited to, a defibrillation shock, a synchronized cardioversion and a transcutaneous pacing.

By the inventive principles of the present invention, primary therapy module 30 serves as a primary medical module for executing primary medical tasks, such as, for example electrical therapy (ies) and remote monitor module 20 serves as a remote medical module for executing remote medical tasks, such as, for example, patient parameter monitoring. More particularly, remote power source 24 may be conditionally charged by primary power source 34 upon the power connection of power interfaces 25 and 35 of respective modules 20 and 30.

A necessary condition is primary power source 34 having sufficient power to remotely charge remote power source 24 in addition to executing the electrical therapy(ies) by primary therapy module 30 based on a power condition of of primary power source 34 and/or whether primary power source 34 is power connected to an external power source 40 or a battery-powered base station (not shown).

An optional condition is remote power source 24 having insufficient power to execute the patient parameter monitoring by remote monitor module 20 based on a power condition of remote power source 24 and/or whether remote power source 24 is power connected to external power source 40 or a battery-powered base station (not shown).

Specifically, remote monitor module 20 incorporates:
(1) a display 21 for textually and/or graphically showing patient parameter measurement(s),
(2) an user interface 22 for selectively controlling the execution and/or display of the patient parameter measurement(s),
(3) a monitor controller 23 for automatically and/or user control measurement(s) of the patient parameter(s), and
(4) remote power source 24 (e.g., rechargeable battery(ies), non-rechargeable battery(ies) and/or a power supply).

Therapy monitoring module 30 incorporates:
(1) a display 31 for textually and/or graphically showing alarm and/or therapy delivery status,
(2) an user interface 32 for selectively controlling an execution and/or the display of the electrical therapy (ies),
(3) a therapy controller 33 for automatically and/or user control execution of the electrical therapy (ies), and
(4) primary power source 34 (e.g., rechargeable battery (ies), non-rechargeable battery(ies) and/or a power supply).

Figure 2:
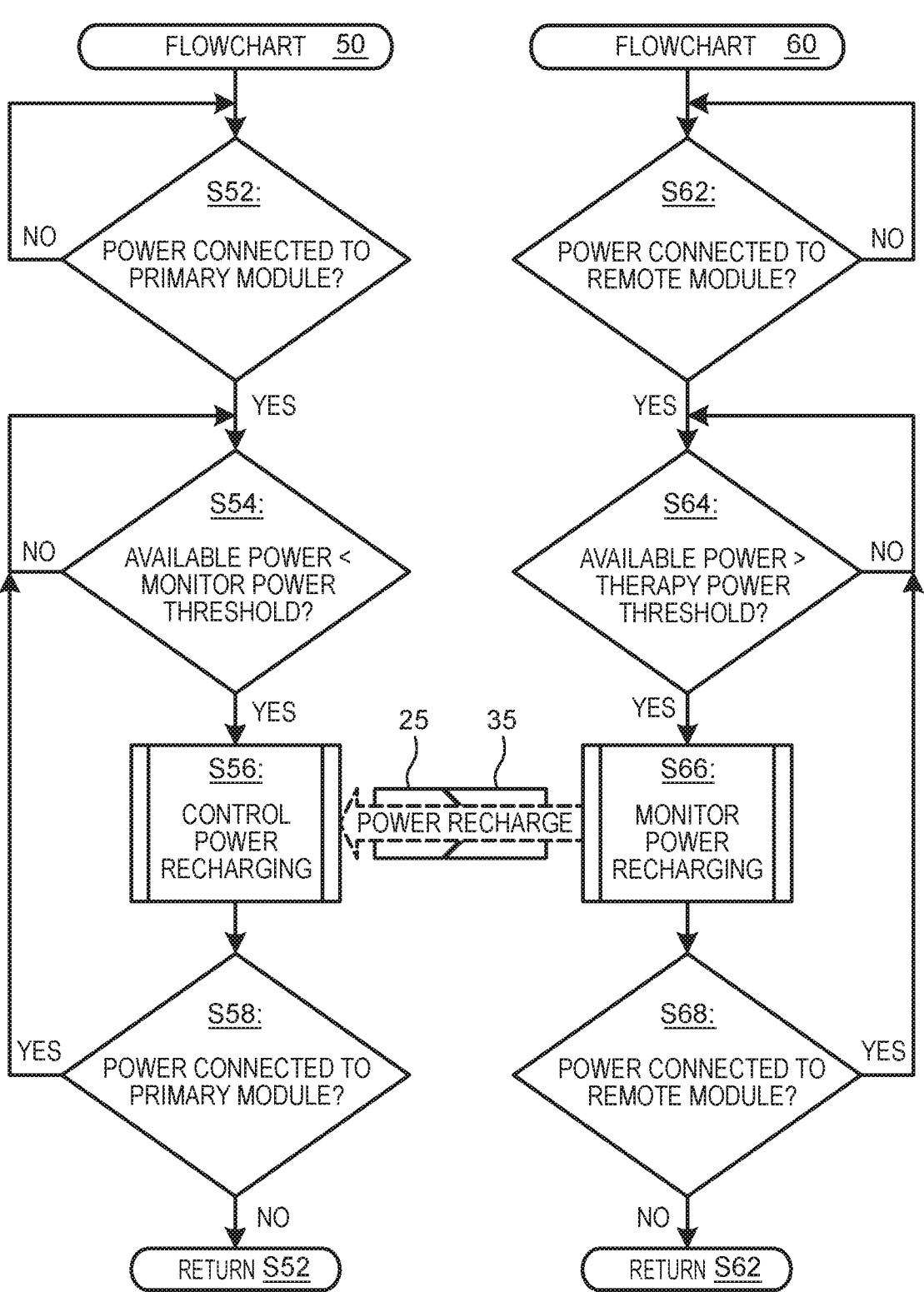
FIG. 2 illustrates flowcharts representative of a power charging method in accordance with the inventive principles of the present invention.

Controllers 23 and 33 are additionally configured to implement a power charging method of the present invention as represented by flowchart 50 and 60 shown in FIG. 2.

Referring to FIGS. 1 and 2, a stage S52 of flowchart 50 and a stage S62 of flowchart 60 encompass controllers 23 and 33 ascertaining if respective modules 20 and 30 are power connected via power interfaces 25 and 35. In practice, power interfaces 25 and 35 may be configured in accordance with various known power connection techniques including, but not limited to, a physical electrical coupling (e.g., a cable or a docking station 36 as shown in FIG. 1) or an inductive coupling. Additionally, controllers 23 and 33 may incorporate known techniques for wired and/or wireless data exchange between controllers 23 and 33 including an acknowledged power connection/disconnection status.

If a power connection exists between modules 20 and 30, a stage S54 of flowchart 50 encompasses monitor controller 23 ascertaining if an available power from remote power source 24 is sufficient or insufficient for monitor controller 23 to execute the patient parameter monitoring based on a power condition of remote power source 24 relative to a monitor power threshold for executing the patient parameter measurement(s) and/or power condition(s) of any external power source 40 or battery-powered base station connected to remote power source 24 relative to the monitor power threshold.

Concurrently, a stage S64 of flowchart 60 encompasses therapy controller 33 ascertaining if an available power from primary power source 34 is sufficient or insufficient for therapy controller 33 to execute the electrical therapy(ies) based on a power condition of primary power source 34 relative to a therapy power threshold for executing the electrical therapy(ies) and/or power condition(s) of any external power source 40 or battery-powered base station connected to primary power source 34 relative to the therapy power threshold.

If the available power from primary power source 34 is insufficient for therapy controller 33 to execute the electrical therapy(ies), then therapy controller 33 proceeds to a stage S66 of flowchart 60 to disable any power charge (e.g., a current draw, a voltage ramping, etc.) from primary power source 34 to remote power source 24 as controlled by monitor controller 23. In practice, the disabling of the power draw may be implemented in various known techniques including, but not limited to, an activation of a relay to open a switch of therapy controller 33 within a circuit path extending between applicable terminal(s) of remote power source 24 and primary power source 34.

If the available power from primary power source 34 is sufficient for therapy controller 33 to execute the electrical therapy(ies), then therapy controller 33 proceeds to a stage S66 of flowchart 60 to enable a power charge (e.g., a current draw, a voltage ramping, etc.) from primary power source 34 to remote power source 24 as controlled by monitor controller 23. In practice, the enabling of the power charge may be implemented in various known techniques including, but not limited to, an activation of a relay to close the switch of therapy controller 33 within a circuit path extending between applicable terminal(s) of remote power source 24 and primary power source 34.

If available power from remote power source 24 is insufficient for monitor controller 23 to execute the patient parameter measurement(s) concurrent to the sufficient available power of primary power source 34, then monitor controller 23 proceeds to a stage S56 of flowchart 50 to control a power charge from primary power source 34 to remote power source 24 as controlled by monitor controller 23. In practice, the control of the power charge may be implemented in various known techniques including, but not limited to, a control of a variable resistor within the circuit path extending between applicable terminal(s) of remote power source 24 and primary power source 34.

The monitor power charging of stages S56 and S66 is maintained until:

(1) modules 20 and 30 are power disconnected as ascertained during respective stages S58 and S68;

(2) monitor controller 23 ascertains upon a return to stage S54 that the available power from remote power source 24 is sufficient for monitor controller 23 to execute the patient parameter monitoring; and (3) therapy controller 33 ascertains upon a return to stage S64 that the available power from primary power source 34 is insufficient for therapy controller 33 to execute the electrical therapy(ies).

Referring to FIGS. 1 and 2, those having ordinary skill in the art will appreciate flowcharts 50 and 60 facilitate a charging of remote power source 24 by primary power source 34 as conditionally established by therapy controller 30 and conditionally controlled by monitor controller 23.

Referring to FIGS. 1 and 2, those having ordinary skill in the art will further appreciate numerous benefits of the present invention including, but not limited to:

(1) Multiple Power charging. A technique for conditionally charging multiple remote medical modules from a single primary medical module, such as, for example, a conditionally charging of a monitoring unit and a patient box by a defibrillator/pacer unit of the Corpuls $C^3$; and (2) Design Tradeoffs. There are many tradeoffs to consider in the design of power sources for medical modules for a modular medical device. For example, to provide for long operating times, a battery must be large and heavy. However, a smaller and lighter battery makes it easier to carry a monitor module, especially when transporting the patient and continued monitoring of the patient's vital parameters is needed. More particularly, a battery for a therapy module must provide a high current discharge rate to rapidly deliver a high-energy electrical shock whereby the high current discharge rate tends to make the battery larger and heavier. The power charging technique of the present invention facilitates a size and weight of the monitoring module's battery being smaller and lighter as compared to a battery of a therapy module whereby the monitoring module may more easily be handled and attached to and carried on a stretcher with the patient.

Furthermore, as one having ordinary skill in the art will appreciate in view of the teachings provided herein, features, elements, components, etc. described in the present disclosure/specification and/or depicted in the FIGS. 1 and 2 may be implemented in various combinations of electronic components/circuitry, hardware, executable software and executable firmware, particularly of a controller as described herein, and provide functions which may be combined in a single element or multiple elements. For example, the functions of the various features, elements, components, etc. shown/illustrated/depicted in the FIGS. 1 and 2 can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, circuitry, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present invention can take the form of a computer program product or application module accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk-read only memory (CD-ROM), compact disk-read/write (CD-R/W) and DVD. Further, it should be understood that any new computer-readable medium which may hereafter be developed should also be considered as computer-readable medium as may be used or referred to in accordance with exemplary embodiments of the present invention and disclosure.

Having described preferred and exemplary embodiments of novel and inventive system and method for power charging a modular medical device, (which embodiments are intended to be illustrative and not limiting), it is noted that modifications and variations can be made by persons having ordinary skill in the art in light of the teachings provided herein, including the FIGS. 1 and 2. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present invention. Further, corresponding and/or related method for manufacturing and/or using a device and/or system in accordance with the present disclosure are also contemplated and considered to be within the scope of the present invention.

The invention claimed is:

1. A modular medical device for a modular execution of a plurality of medical tasks, the modular medical device comprising:
   a primary medical module for executing a primary medical task, wherein the primary medical module includes:
      a primary power source for powering an execution of the primary medical task by the primary medical module; and
      a primary medical controller configured to ascertain if the primary power source has sufficient power or insufficient power for powering the execution of the primary medical task by the primary medical module; and
   a remote medical module for executing a remote medical task, wherein the remote medical module includes:
      a remote power source for powering an execution of the remote medical task by the remote medical module; and
      a remote medical controller,
         wherein the primary medical controller is further configured to enable the remote medical controller to control a power charging of the remote power source by the primary power source across a power connection between the primary medical module and the remote medical module responsive to the primary medical controller ascertaining the primary power source has sufficient power for powering the execution of the primary medical task by the primary medical module, and
         wherein the remote medical controller is configured to control the power charging of the remote power source by the primary power source across the power connection between the primary medical module and the remote medical module when the primary medical controller enables the remote medical controller to control the power charging of the remote power source by the primary power source across the power connection between the primary medical module and the remote medical module.

2. The modular medical device of claim 1, wherein the remote medical controller configured to control the power charging of the remote power source by the primary power source across the power connection between the primary medical module and the remote medical module includes:
   the remote medical controller configured to ascertain if the remote power source has sufficient power or insufficient power for powering the execution of the remote medical task by the remote medical module;
   the remote medical controller configured to initiate the power charging of the remote power source by the primary power source across the power connection between the primary medical module and the remote medical module responsive to the remote medical module ascertaining the remote power source has insufficient power for powering the execution of the remote medical task assigned to the remote medical module; and
   the remote medical controller configured to terminate the power charging of the remote power source by the primary power source across the power connection between the primary medical module and the remote medical module responsive to the remote medical module subsequently ascertaining the remote power source has sufficient power for powering the execution of the remote medical task assigned to the remote medical module.

3. The modular medical device of claim 1, wherein the primary medical controller is further configured to prevent the remote medical controller from controlling the power charging of the remote power source by the primary power source across the power connection between the primary medical module and the remote medical module responsive to the primary medical controller ascertaining the primary power source has insufficient power for powering the execution of the primary medical task by the primary medical module previous to the primary medical controller ascertaining the primary power source has sufficient power for powering the execution of the primary medical task by the primary medical module.

4. The modular medical device of claim 1, wherein the primary medical controller is further configured to terminate the remote medical controller from controlling the power charging of the remote power source by the primary power source across the power connection between the primary medical module and the remote medical module as con- trolled by the remote medical module responsive to the primary medical controller ascertaining the primary power source has insufficient power for powering the execution of the primary medical task by the primary medical module subsequent to the primary medical controller ascertaining the primary power source has sufficient power for powering the execution of the primary medical task by the primary medical module.

5. The modular medical device of claim 1, wherein the primary power source includes at least one of a rechargeable battery, a non-rechargeable battery or a power supply.

6. The modular medical device of claim 1, wherein the primary medical controller is further configured to connect the primary power source to an external power source.

7. The modular medical device of claim 1, wherein the remote power source includes at least one of a rechargeable battery, a non-rechargeable battery or a power supply.

8. The modular medical device of claim 1, wherein the primary medical task is an electrical therapy task.

9. The modular medical device of claim 1, wherein the remote medical task is a patient parameter monitoring task.

* * * * *